United States Patent [19]

Chen

[11] 4,237,054
[45] Dec. 2, 1980

[54] TOTAL SYNTHESIS OF (1RS,4SR,5RS)-4-(4,8-DIMETHYL-5-HYDROXY-7-NONENYL)-4-METHYL-3,8-DIOXABICYCLO[3.2.1] OCTANE-1-ACETIC ACID

[75] Inventor: Robert H. K. Chen, Belle Mead, N.J.

[73] Assignee: Ortho Pharmaceutical Corporation, Raritan, N.J.

[21] Appl. No.: 40,346

[22] Filed: May 18, 1979

[51] Int. Cl.$^3$ .................................................. C07D 319/00
[52] U.S. Cl. ........................... 260/340.6; 260/340.9 R; 260/345.9 R; 260/348.25; 560/156; 560/177
[58] Field of Search ....................................... 260/340.6

[56] References Cited

U.S. PATENT DOCUMENTS 4,102,895   7/1978   Kanojia et al. ................... 260/340.6

OTHER PUBLICATIONS

Cram & Hammond, Organic Chemistry, p. 355, 1964 2nd Edition.

*Primary Examiner*—Ethel G. Love
*Attorney, Agent, or Firm*—Benjamin F. Lambert

[57] ABSTRACT

A method for the total synthesis of (1RS,4SR,5RS)-4-(4,8-dimethyl-5-hydroxy-7-nonenyl)-4-methyl-3,8-dioxabicyclo [3.2.1] octane-1-acetic acid is described. The compound is active as a utero-evacuant agent.

11 Claims, No Drawings

TOTAL SYNTHESIS OF (1RS,4SR,5RS)-4-(4,8-DIMETHYL-5-HYDROXY-7-NONENYL)-4-METHYL-3,8-DIOXABICYCLO[3.2.1] OCTANE-1-ACETIC ACID

The present invention relates to a method for the total synthesis of (1RS,4SR,5RS)-4-(4,8-dimethyl-5-hydroxy-7-nonenyl)-4-methyl-3,8-dioxabicyclo [3.2.1] octane-1-acetic acid. The compound and its preparation from the naturally occurring compound known as zoapatanol are described in U.S. Pat. No. 4,102,895 and has the following structure:

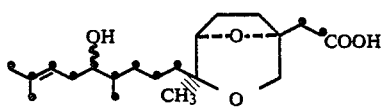

The bicyclic compound is active as a utero-evacuant agent.

The synthesis is comprised of several steps which are summarized in the following schematic diagram:

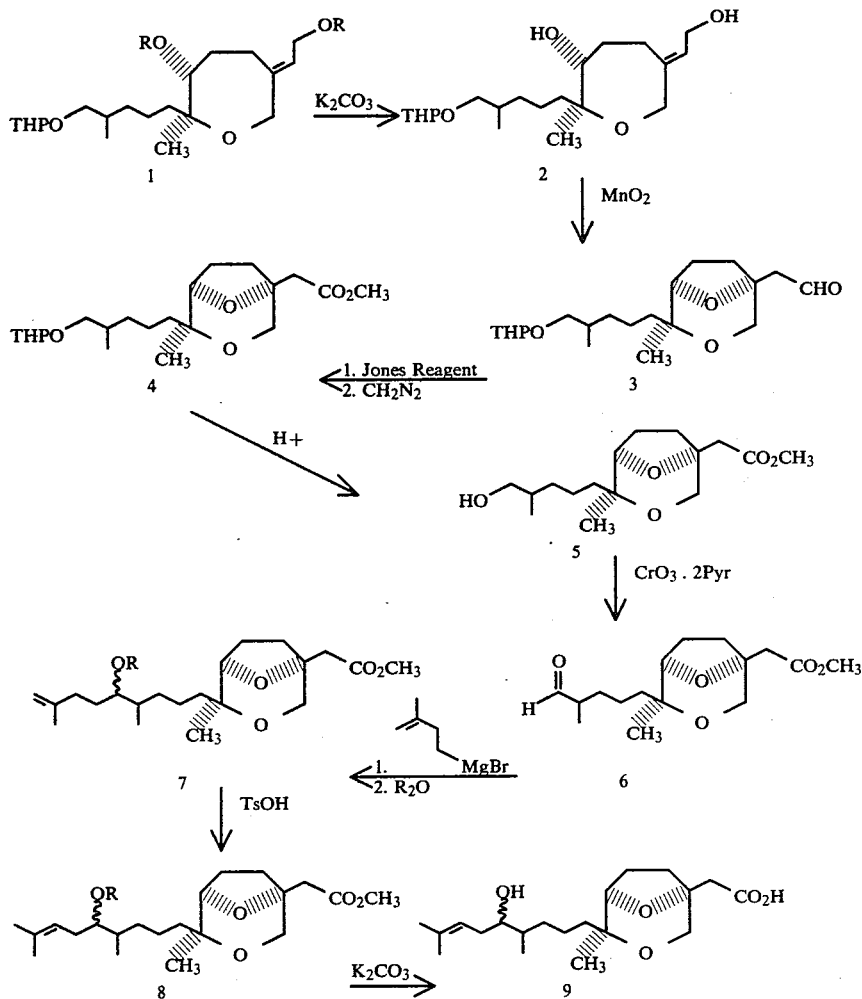

wherein R is lower alkanoyl having 2–5 carbon atoms such as an acetyl or propionyl group, for example, and TsOH is p-toluenesulfonic acid.

As can be seen from the diagram, the first step in the synthesis involves the hydrolysis of the diester 5-[(2RS,3SR)-3-acetoxy-6-[(E)-2-acetoxyethylidene]-2-methyl-2-oxepanyl]-2-methyl-1-tetrahydropyran-2-yloxy pentane (1) to the corresponding diol (2). The hydrolysis is carried out by reaction with a mild base such as dilute sodium hydroxide, potassium carbonate or sodium carbonate in a suitable solvent such as, for example, ethanol-water, methanol-water and dioxane-water. The reaction is preferably carried out at room temperature and the diol is isolated by techniques known to those skilled in the art.

In the second step in the synthesis, the diol (2) is reacted with an oxidizing agent such as manganese dioxide to form the bicyclic aldehyde (3). Generally an excess of the oxidizing agent is employed in the oxidation step. Examples of solvents which can be employed include methylene chloride and chloroform. Reaction of the bicyclic aldehyde (3) with Jones reagent in a suitable solvent such as acetone or 2-butanone, for example, gives a crude acid which is not isolated but is treated with an excess of diazomethane in a suitable solvent such as ether or tetrahydrofuran to form the methyl ester (4). The reaction with Jones reagent is preferably carried out at a temperature between $-70°–0°$ C. while the reaction with diazomethane is preferably carried out at room temperature.

Acid hydrolysis of the methyl ester (4) yields the primary alcohol (5). The hydrolysis is preferably carried out in a mixture of tetrahydrofuran-water-acetic acid at a temperature of about 60° C. Other solvent systems which can be employed include methanol-p-toluenesulfonic acid and ethanol-p-toluenesulfonic acid. Oxidation of the primary alcohol with the chromium trioxide-pyridine complex gives the corresponding aldehyde (6). The oxidation is carried out in a suitable solvent such as methylene chloride or chloroform and preferably at a temperature between $-20°-0°$ C. It is preferred to use an excess of the complex.

Treatment of the aldehyde (6) with 3-methyl-3-butenyl magnesium bromide in a suitable solvent such as tetrahydrofuran or ether followed by an excess of an acid anhydride such as acetic anhydride, propionic anhydride, or butyric anhydride, for example, yields the corresponding ester (7). The ester is purified by techniques known to those skilled in the art such as column chromatography over an adsorbent material such as silica gel, florisil or alumina. Isomerization of the ester (7) with p-toluenesulfonic acid monohydrate in a suitable solvent such as benzene or toluene at a temperature between 50°–100° C. yields the isomeric compound (8). The reaction is preferably carried out at the reflux temperature of the solvent. Hydrolysis of the ester with a mild base such as potassium carbonate, sodium hydroxide or sodium bicarbonate followed by acidification with an acid such as hydrochloric acid or sulfuric acid at room temperature yields the free acid (9). The acid is purified by techniques known to those skilled in the art such as, for example, column chromatography over a suitable adsorbent material such as silica gel, alumina or florisil.

The starting material in the synthesis of the bicyclo compound, the diester 5-[(2RS,3SR)-3-acetoxy-6-[(E)-2-acetoxyethylidene]-2-methyl-2-oxepanyl]-2-methyl-1-(tetrahydropyran-2-yloxy)pentane is prepared according to the method described in copending application Ser. No. 920,433 filed June 29, 1978.

The following examples describe the invention in greater detail and are intended to be a way of illustrating but not limiting the invention.

EXAMPLE 1

5-[(2RS,3SR)-3-Hydroxy-6-[(E)-2-hydroxyethylidene]-2-methyl-2-oxepanyl]-2-methyl-1-(tetrahydropyran-2-yloxy)pentane (2)

A mixture of 5-[(2RS,3SR)-3-acetoxy-6-[(E)-2-acetoxyethylidene]-2-methyl-2-oxepanyl]-2-methyl-1-(tetrahydropyran-2-yloxy)pentane (1.2 g, 2.73 mM), methanol (10 ml) and saturated potassium carbonate (1 ml) and water (1 ml) is stirred under nitrogen at room temperature for three hours. Most of the solvent is removed in vacuo to give a thick oil. This crude material is filtered through a silica gel column (15 g) and washed with ether (100 ml). The solvent is removed in vacuo to give 5-[(2RS,3SR)-3-hydroxy-6-[(E)-2-hydroxyethylidene]-2-methyl-2-oxepanyl]-2-methyl-1-(tetrahydropyran-2-yloxy)pentane (0.953 g, 87%) as a colorless oil.

IR (neat): 3450 cm$^{-1}$

NMR (CDCl$_3$)δ: 0.97 (d, J=6 Hz, 3H,

1.21 (s, 3H,

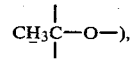

5.41 (bt, J=6 Hz, 1H,

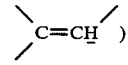

EXAMPLE 2

(1RS,4SR,5RS)-4-Methyl-4-[4-methyl-5-(tetrahydropyran-2-yloxy)pentyl]-3,8-dioxabicyclo [3.2.1] octane-1-acetaldehyde (3)

A mixture of 5-[(2RS,3SR)-3-hydroxy-6-[(E)-2-hydroxyethylidene]-2-methyl-2-oxepanyl]-2-methyl-1-(tetrahydropyran-2-yloxy)pentane (953 mg, 2.67 mM), manganese dioxide (4 g) and methylene chloride (20 ml) is stirred for three days at room temperature under nitrogen. The mixture is filtered through a pad of Celite and washed with methylene chloride (2×30 ml). The solvent is removed in vacuo and the residue purified by column chromatography on silica gel (15 g) with 30% ether in petroleum ether to give (1RS,4SR,5RS)-4-methyl-4-[4-methyl-5-(tetrahydropyran-2-yloxy)pentyl]-3,8-dioxabicyclo [3.2.1] octane-1-acetaldehyde (0.813 g, 73%) as a colorless oil.

IR (neat): 1735 cm$^{-1}$

NMR (CDCl$_3$)δ: 0.92 (d, J=6 Hz, 3H,

1.35 (s, 3H,

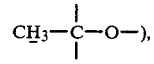

2.6 (d, J=2.4 Hz, 2H, —CH$_2$CHO), 9.9 (t, J=2.4 Hz, 1H, —CH$_2$CHO)

EXAMPLE 3

Methyl (1RS,4SR,5RS)-4-methyl-4-[4-methyl-5-(tetrahydropyran-2-yloxy)pentyl]-3,8-dioxabicyclo [3.2.1] octane-1-acetate (4)

An excess of Jones reagent (4 ml, 4 mM) is added slowly to a mixture of (1RS,4SR,5RS)-4-methyl-4-[4-methyl-5-(tetrahydropyran-2-yloxy)pentyl]-3,8-dioxabicyclo [3.2.1] octane-1-acetaldehyde (813 mg, 2.3 mM) and acetone (20 ml) at 0° C. The resulting mixture is stirred for thirty minutes and treated with 2-propanol (2 ml) followed by ethyl acetate (50 ml) and water (20 ml). The organic layer is separated and the aqueous layer is extracted with ethyl acetate (3×20 ml). The combined organic layers are dried (sodium sulfate) and the solvent is removed in vacuo to give a pale yellow oil. The oil is redissolved in ether (15 ml), treated with an excess of diazomethane in ether and stirred for ten minutes. The solvent is removed in vacuo to give methyl (1RS,4SR,5RS)-4-methyl-4-[4-methyl-5-(tetrahydropyran-2-yloxy)pentyl]-3,8-dioxabicyclo [3.2.1] octane-1-acetate as a pale yellow oil (625 mg, 83%). This material is homogeneous by thin layer chromatography and is used directly in the next step.

EXAMPLE 4

Methyl (1RS,4SR,5RS)-4-(5-hydroxy-4-methylpentyl)-4-methyl-3,8-dioxabicyclo [3.2.1] octane-1-acetate (5)

A mixture of methyl (1RS,4SR,5RS)-4-methyl-4-[4-methyl-5-tetrahydropyran-2-yloxy)pentyl]-3,8-dioxabicyclo [3.2.1] octane-1-acetate (625 mg, 1.89 mM), tetrahydrofuran (1 ml), water (1 ml) and acetic acid (4 ml) is heated at 60° C. for 4.5 hours under nitrogen. The mixture is cooled to room temperature and most of the solvent is removed in vacuo. The residue is filtered through a small silica gel column (5 g) and washed with ether (100 ml). The solvent is removed in vacuo to give methyl (1RS,4SR,5RS)-4-(5-hydroxy-4-methylpentyl)-4-methyl-3,8-dioxabicyclo [3.2.1] octane-1-acetate (430 mg, 78%) as a colorless oil.

IR (neat): 3340 and 1745 cm$^{-1}$
NMR (CDCl$_3$)δ: 0.93 (d, J=6 Hz, 3H,

CH$_3$C$\underline{H}$), 1.37 (s, 3H,

CH$_3$C$-$O$-$), 2.6 (s, 2H, $-$C$\underline{H}_2$CO$_2$CH$_3$), 3.66 (s, 3H, $-$CO$_2$C$\underline{H}_3$)

EXAMPLE 5

Methyl (1RS,4SR,5RS)-4-methyl-4-(4-methyl-5-oxopentyl)-3,8-dioxabicyclo [3.2.1] octane-1-acetate (6)

A mixture of methyl (1RS,4SR,5RS)-4-(5-hydroxy-4-methyl-pentyl)-3,8-dioxabicyclo [3.2.1] octane-1-acetate (420 mg, 1.4 mM) and methylene chloride (5 ml) is added to a mixture of chromium trioxide-pyridine complex (10 mM), methylene chloride (20 ml) and Celite (2 g) at 0° C. and stirred for four hours under nitrogen. The resulting mixture is filtered and washed with ether (100 ml). The filtrate is treated with ether (200 ml) and washed with saturated sodium bicarbonate solution (3×100 ml), saturated cupric sulfate solution (2×100 ml) and dried (sodium sulfate). The solvent is removed in vacuo to give methyl (1RS,4SR,5RS)-4-methyl-4-(4-methyl-5-oxopentyl)-3,8-dioxabicyclo [3.2.1] octane-1-acetate as a colorless oil. This material is homogeneous by thin layer chromatography.

IR (neat): 2710 and 1740 (broad) cm$^{-1}$

EXAMPLE 6

Methyl (1RS,4SR,5RS)-4-(5-acetoxy-4,8-dimethyl-8-nonenyl)-4-methyl-3,8-dioxabicyclo [3.2.1] octane-1-acetate (7)

3-Methyl-3-butenyl magnesium bromide in tetrahydrofuran (0.9 ml, 1 mM) is added to a mixture of methyl (1RS,4SR,5RS)-4-methyl-4-methyl-4-(4-methyl-5-oxopentyl)-3,8-dioxabicyclo [3.2.1] octane-1-acetate (310 mg, 1.04 mM) at $-78°$ C. under nitrogen. After the addition is complete, the mixture is allowed to warm to room temperature, and stirred for two hours. The resulting mixture is treated with acetic anhydride (0.5 ml) and stirred overnight. The reaction mixture is cooled to 0° C. and saturated ammonium chloride solution (10 ml) is added. The mixture is then extracted with ether (3×50 ml). The organic layers are combined, dried (sodium sulfate), and the solvent is removed in vacuo. The residue is purified by column chromatography on silica gel (30 g) with 30% ether in petroleum ether to give methyl (1RS,4SR,5RS)-4-(5-acetoxy-4,8-dimethyl-8-nonenyl)-4-methyl-3,8-dioxabicyclo [3.2.1] octane-1-acetate (270 mg, 65%) as a colorless oil.

IR (neat): 1745 and 1250 cm$^{-1}$
NMR (CDCl$_3$)δ: 0.95 (d, J=6 Hz, 3H,

CH$_3$C$\underline{H}$), 1.38 (s, 3H,

CH$_3$C$-$O$-$), 2.01 (s, 3H, C$\underline{H}_3$CO$_2-$), 2.6 (s, 2H, $-$C$\underline{H}_2$CO$_2$CH$_3$), 3.7 (s, 3H, $-$CH$_2$CO$_2$C$\underline{H}_3$), 5.64 (bs, 2H,

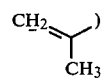

EXAMPLE 7

Methyl (1RS,4SR,5RS)-4-(5-acetoxy-4,8-dimethyl-7-nonenyl)-4-methyl-3,8-dioxabicyclo [3.2.1] octane-1-acetate (8)

A mixture of methyl (1RS,4SR,5RS)-4-(5-acetoxy-4,8-dimethyl-8-nonenyl)-4-methyl-3,8-dioxabicyclo [3.2.1] octane-1-acetate (93 mg, 0.24 mM), benzene (6 ml) and p-toluenesulfonic acid monohydrate (1 crystal) is heated to 80° C. for sixteen hours under nitrogen. The resulting mixture is cooled to room temperature and treated with ether (100 ml). The organic phase is washed with 5% sodium bicarbonate solution (5 ml) and dried (sodium sulfate). The solvent is removed in vacuo to give methyl (1RS,4SR,5RS)-4-(5-acetoxy-4,8-dimethyl-7-nonenyl)-4-methyl-3,8-dioxabicyclo [3.2.1] octane-1-acetate (72 mg, 90%) as a colorless oil. This material is homogeneous by thin layer chromatography and is used directely in the next step.

EXAMPLE 8

(1RS,4SR,5RS)-4-(4,8-Dimethyl-5-hydroxy-7-nonenyl)-4-methyl-3,8-dioxabicyclo [3.2.1] octane-1-acetic acid (9)

A mixture of methyl (1RS,4SR,5RS)-4-(5-acetoxy-4,8-dimethyl-7-nonenyl)-4-methyl-3,8-dioxabicyclo [3.2.1] octane-1-acetate (132 mg, 0.31 mM), methanol (5 ml), saturated potassium carbonate solution (2 ml) and water (1 ml) is stirred at room temperature for three days under nitrogen. The mixture is cooled to 0° C. and acidified to pH 1 with 10% hydrochloric acid and then extracted with ethyl acetate (3×15 ml). The combined organic layers are dried (sodium sulfate) and the solvent is removed in vacuo to give a pale yellow oil (100 mg). This material is purified by column chromatography on silica gel (5 g) with ether to give (1RS,4SR,5RS)-4-(4,8-dimethyl-5-hydroxy-7-nonenyl)-4-methyl-3,8-dioxabicyclo [3.2.1] octane-1-acetic acid (71 mg, 75%) as a colorless oil. The product obtained by this procedure compares favorably with the derivative of the natural product obtained and characterized in U.S. Pat. No. 4,102,895.

IR (neat): 3460, 1724 cm$^{-1}$
NMR (CDCl$_3$)δ: 0.88 (d, J=7 Hz, 3H,

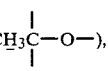

1.31 (s, 3H,

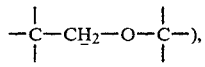

1.63 and 1.71 [each s, each 3H, (C$\underline{H}_3$)$_2$—C=CH—], 2.60 (s, 2H, —C$\underline{H}_2$CO$_2$H), 3.39 and 3.76 (each d, J=11 Hz, 2H,

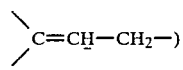

5.16 (bt, J=6 Hz, 1H, $$\diagdown_{\diagup}C=C\underline{H}—CH_2—)$$

Preparation of starting material

EXAMPLE A

3-Methyl-4-(tetrahydropyran-2-yloxy)-1-butene (a) To a suspension of magnesium turnings (50.4 g, 2.1 m) in ether (1500 ml) under a nitrogen atmosphere is added a solution of crotyl bromide (135.0 g, 1.0 m) in ether (125 ml), at room temperature over a period of four hours. The reaction mixture is then cooled to 0° C. and formaldehyde [formed by pyrolysis of paraformaldehyde (45.0 g, 0.5 m)] is bubbled through the mixture. The resulting mixture is allowed to come to room temperature and stirred overnight. The reaction mixture is then decanted into a solution of ammonium chloride (212 g, 4.0 m) in ice water (2 l). The mixture is extracted with ether (2×3000 ml) and the combined ether extracts are dried (Na$_2$SO$_4$) and filtered. The solvent is removed in vacuo to give 57.2 g of 2-methyl-3-buten-1-ol (66%).

NMR (CDCl$_3$)δ: 0.99 (d, J=7 Hz, 3H,

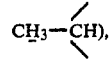

2.10–2.70 (m, 1H,

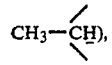

3.30–3.60 (bd, J=6 Hz, 2H,

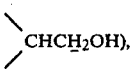

4.83–6.13 (m, 3H, vinyl protons)
IR (neat): 3257, 1640 cm$^{-1}$ (b) A solution of 2-methyl-3-buten-1-ol (54.16 g, 0.63 m), dihydropyran (52.92 g, 0.63 m), and p-toluenesulfonic acid (0.5 g) in ether (800 ml) is stirred at room temperature under a nitrogen atmosphere overnight. The reaction mixture is then diluted with ether (1 l) and washed with 5% sodium bicarbonate solution (1 l). The ether extract is dried (Na$_2$SO$_4$), filtered and solvent removed in vacuo to give 95.8 g of crude product. The crude product is purified by column chromatography on silica gel (500 g, hexane) to give (75%) 3-methyl-4-(tetrahydropyran-2-yloxy)-1-butene (80.62 g).

NMR (CDCl$_3$)δ: 1.05 (d, J=6 Hz, 3H,

CH$_3$C$\underline{H}$), 1.33–2.00

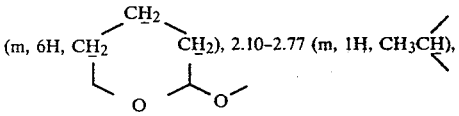

3.03–4.10

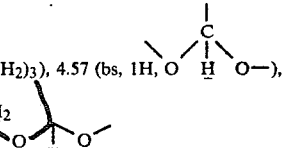

4.77–6.13 (m, 3H, vinyl protons)
IR (neat): 1643 (cm$^{-1}$)

EXAMPLE B

1-Bromo-3-methyl-4-(tetrahydropyran-2-yloxy)-butane

Diborane in tetrahydrofuran (125 ml, 0.150 m) at 0° C. under nitrogen is added to a mixture of 3-methyl-4-(tetrahydropyran-2-yloxy)-1-butene (72 g, 0.423 m) and tetrahydrofuran (150 ml). After the addition is complete, the mixture is allowed to warm to room temperature and then stirred for 1 hour. The reaction mixture is cooled to 0° C. and bromine (24 ml, 0.43 mmole) and sodium methoxide (0.565 m) in methanol (300 ml) are added slowly simultaneously. After the addition is complete, the mixture is allowed to warm to room temperature and stirred for thirty minutes. The mixture is then treated with water (100 ml) and extracted with petroleum ether (2×200 ml). The organic layer is washed with 5% sodium bicarbonate (100 ml), water (2×100 ml) and dried (Na$_2$SO$_4$). The solvent is removed in vacuo to give a colorless liquid. This crude product is purified by column chromatography on silica gel (500 g, 1% ether in petroleum ether) to give 1-bromo-3-methyl-4-(tetrahydropyran-2-yloxy)-butane (71 g, 65%) as a colorless liquid. NMR (CDCl$_3$)δ: 1.0 (d, J=6 Hz, 3H,

4.59 (br, 1H,

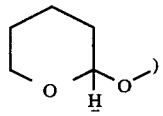

EXAMPLE C

1-Acetoxy-3-acetoxymethyl-7,11-dimethyl-6,7-oxido-12-(tetrahydropyran-2-yloxy)-2-(E)-dodecene 1-Bromo-3-methyl-4-(tetrahydropyran-2-yloxy)-butane (20 g, 80 mmole) is added to a suspension of magnesium turnings (2.4 g, 100 mmole) in tetrahydrofuran (100 ml) at room temperature under nitrogen over a period of four hours.

An excess of the Grignard reagent prepared above is added to a solution of 7-methyl-3-hydroxymethyl-6,7-oxido-8-tosyloxy-(E)-2-octen-1-ol (950 mg, 2.67 mmole) in tetrahydrofuran (5 ml) followed by Li$_2$CuCl$_4$ (0.1 mmole) at 0° C. and the resulting mixture is stirred for four hours. The mixture is allowed to warm to room temperature treated with acetic anhydride (2 ml) and stirred overnight. The solvent is removed in vacuo and the residue is purified by column chromatography on silica gel (30 g, 40% ether in petroleum ether) to give 1-acetoxy-3-acetoxymethyl-7,11-dimethyl-6,7-oxido-12-(tetrahydropyran-2-yloxy)-2-(E)-dodecene (301 mg. 25%) as a colorless oil.

IR (neat): 1735 cm$^{-1}$

NMR (CDCl$_3$)δ: 0.95 (d, J=6 Hz, 3H,

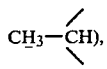

1.04 (s, 3H,

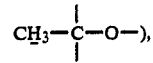

2.02 and 2.04 (both s, 6H, C$\underline{H}_3$CO$_2$—), 2.64 (bt, J=6 Hz, 1H,

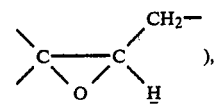

5.61 (bt, J=6 Hz, 1H,

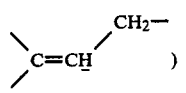

EXAMPLE D

5-[(2RS,3SR)-3-Acetoxy-6-[(E)-2-acetoxyethylidene]-2-methyl-2-oxepanyl]-2-methyl-1-(tetrahydropyran-2-yloxy)-pentane A mixture of 1-acetoxy-3-acetoxymethyl-7,11-dimethyl-6,7-oxido-12-(tetrahydropyran-2-yloxy)-2-(E)-dodecene (512 mg, 1.16 mmole), methanol (20 ml) and saturated potassium carbonate (1 ml) is stirred at room temperature for 4 hours under nitrogen. Most of the solvent is removed in vacuo and the residue is filtered through a silica gel column (10 g) and washed with ether (100 ml). The solvent is removed in vacuo to give the compound 3-hydroxymethyl-7,11-dimethyl-6,7-oxido-12-(tetrahydropyran-2-yloxy)-2(E)-dodecen-1-ol (410 mg) as a colorless oil. The oil is redissolved in methylene chloride (20 ml) and treated with trifluoroacetic acid (2 drops). The resulting mixture is stirred for 30 minutes, treated with pyridine (2 ml) and acetic anhydride (1.5 ml) and allowed to stir overnight. The solvent is removed in vacuo and the residue is purified by column chromatography on silica gel (10 g, 25% ether in petroleum ether) to give 5-[2RS,3SR)-3-acetoxy-6-[(E)-2-acetoxyethylidene]-2-methyl-2-oxepanyl]-2-methyl-1-tetrahydropyran-2-yloxy)-pentane (130 mg, 25%) as a colorless oil.

IR (neat): 1735 cm$^{-1}$;

NMR (CDCl$_3$)δ: 0.95 (d, J=6 Hz, 3H,

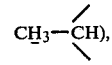

1.15 (s, 3H,

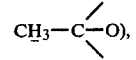

2.02 (s, 6H, C$\underline{H}_3$CO$_2$—), 4.10 (bs, 2H,

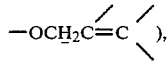

5.41 (bt, J=6 Hz, 1H, C=CH—CH₂OAc)

EXAMPLE E

Methyl 3-methyl-4-nitrobutanoate 1,5-Diazabicyclo[5,4,0]undec-5-ene (6 ml) is added to a solution of nitromethane (91.5 g) in methanol (500 ml). The resulting mixture is heated to 60° C. and methyl crotonate (100 g, 1 m) is added under nitrogen. The mixture is then stirred for 6 days at 60° C. after which it is cooled to room temperature and most of the methanol is removed in vacuo. The residue is treated with ether (500 ml) and washed with 2N hydrochloric acid (250 ml) and water (250 ml). The organic layer is dried (Na₂SO₄) and evaporated in vacuo to give crude product. The crude product is purified by column chromatography on silica gel (500 g, ethyl acetate/hexane 2:98) to give methyl 3-methyl-4-nitrobutanoate (106.6 g, 66%).

IR (neat) 1735 and 1550 cm⁻¹

NMR (CDCl₃)β: 0.95 (d, J=6 Hz, 3H,

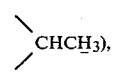

3.68 (s, 3H, —CO₂CH₃), 4.42 (pair of doublets, J=6 Hz each, 2H,

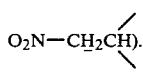

EXAMPLE F

Methyl 3-methyl-4-oxo-butanoate (a) A solution of methyl 3-methyl-4-nitrobutanoate (24.55 g) in methanol (10 ml) is added dropwise to a solution of sodium methoxide (6.37 g) in methanol (250 ml) at room temperature under nitrogen. The resulting mixture is stirred for one hour, added to a mixture of 20% titanous chloride (170 ml), and pH 7 buffer (potassium phosphate monobasic—sodium hydroxide buffer) solution (340 ml) and stirred for 30 minutes. The mixture is then treated with ether (1 l). The organic phase is separated, dried (Na₂SO₄) and evaporated in vacuo to give the crude product. The crude material is purified by column chromatography on silica gel (300 g, 2% ethyl acetate in hexane) to give methyl 3-methyl-4-oxo-butanoate as a colorless liquid. This material is used directly in the next step.

(b) A solution of methyl 3-methyl-4-nitrobutanoate (96 g, 0.596 m) in methanol (30 ml) is added dropwise to a solution of sodium methoxide (34.5 g, 0.638 m) in methanol (1 l) at room temperature under nitrogen. The resulting mixture is stirred for 1 hour, cooled to −78° C. and treated with one equivalent of ozone. The reaction mixture is then allowed to warm to room temperature and most of the solvent is removed in vacuo. The residue is filtered and the filtrate is treated with ether (500 ml). The organic phase is washed with water (3×200 ml), dried (Na₂SO₄) and the solvent is removed in vacuo to give the crude product, methyl 3-methyl-4-oxo-butanoate (86.3 g). This material is used directly in the next step.

EXAMPLE G

Methyl 4,4-ethylenedioxy-3-methyl-butanoate

A mixture of methyl 3-methyl-4-oxo-butanoate (86.3 g), ethylene glycol (61.75 g, 0.996 m), p-toluenesulfonic acid (1 g) and benzene (700 ml) is refluxed under nitrogen for 16 hours. The resulting mixture is allowed to cool to room temperature and treated with ether (300 ml). The organic phase is washed with 5% sodium bicarbonate solution (100 ml), dried (Na₂SO₄) and evaporated in vacuo to give methyl 4,4-ethylenedioxy-3-methylbutanoate as a crude product (63.2 g). This material is used directly in the next step.

EXAMPLE H

4,4-Ethylenedioxy-3-methyl-1-butanol

A solution of methyl 4,4-ethylenedioxy-3-methylbutanoate (63.2 g) in ether (200 ml) is added dropwise to a mixture of lithium alumnium hydride (13.8 g, 0.363 m) in ether (500 ml) at 0° C. under nitrogen. The resulting mixture is stirred for 2 hours, treated with 5% sodium bicarbonate solution (100 ml), allowed to warm to room temperature and filtered. The filtrate is dried (Na₂SO₄) and the solvent is evaporated in vacuo to give the crude product (26 g). This material is further purified by column chromatography on silica gel (300 g, 20% ethyl acetate in hexane) to give 4,4-ethylenedioxy-3-methyl-1-butanol as a colorless liquid (14.9 g).

IR (neat) 3440 cm⁻¹,

NMR (CDCl₃)δ: 0.97 (d, J=7 Hz, 3H, —CHCH₃), 3.53–3.88 (m, 6H,

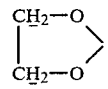

and —CH₂OH), 4.65 (d, J=4 Hz, 1H,

EXAMPLE I

1-Bromo-4,4-ethylenedioxy-3-methyl-butane

A solution of 4,4-ethylenedioxy-3-methyl-1-butanol (30 g, 0.205 m) in triethylamine (75 ml) is added dropwise to a mixture of phosphorous tribromide (63.36 g, 0.228 m) and petroleum ether (100 ml) at room temperature. After the addition is complete, the resulting mixture is heated at 60° C. for 3 hours, cooled to 0° C. and treated with ether (300 ml). The ether mixture is then poured into cold 5% sodium bicarbonate solution (100 ml). The organic phase is separated, dried (Na₂SO₄) and evaporated to give a pale yellow liquid (31 g). The crude product is further purified by column chromatography on silica gel (100 g, 10% ether in petroleum ether) to give 1-bromo-4,4-ethylenedioxy-3-methyl-butane as a colorless liquid (9.9 g, 23%).

NMR (CDCl₃)δ: 0.97 (d, J=7 Hz, 3H,

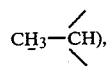

3.50 (bt, J=6 Hz, 2H, —CH$_2$—C$\underline{H}_2$Br), 3.85 (b, 4H, —OC$\underline{H}_2$C$\underline{H}_2$—O—), 4.64 (d, J=4 Hz, 1H,

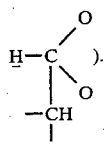

EXAMPLE J

8-Hydroxy-7-methyl-3-methylene-6,7-oxido-1-octene

A solution of sodium acetate (25 g, 0.03 m) in 40% peracetic acid (85 ml) is added to a mixture of 8-hydroxy-7-methyl-3-methylene-1,6(E)-octadiene (50.0 g, 0.33 m), sodium carbonate (42.4 g, 0.40 m) and methylene chloride (500 ml) at 0° C. The resulting mixture is allowed to come to room temperature, stirred for an additional hour and then filtered, diluted with methylene chloride (1 l) and washed with 5% sodium bicarbonate solution (2 l). The organic layer is dried (Na$_2$SO$_4$), and evaporated in vacuo to give 8-hydroxy-7-methyl-3-methylene-6,7-oxido-1-octene as a crude product (49.5 g). The crude product is purified by column chromatography on silica gel (600 g; ethyl acetate/hexane 1:9) to give 8-hydroxy-7-methyl-3-methylene-6,7-oxido-1-octene (23.2 g, 42%).

IR (neat): 3448, 1592 cm$^{-1}$;
NMR (CDCl$_3$)δ: 1.25 (s, 3H,

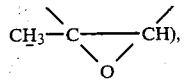

3.03 (t, J=6 Hz, 1H,

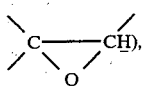

3.56 (s, 2H, —C$\underline{H}_2$—OH), 4.90–6.58 (m, 5H,

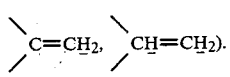

EXAMPLE K

1-Acetoxy-8-hydroxy-7-methyl-3-acetoxymethyl-6,7-oxido-(E)-2-octene

Bromine (56.8 g, 0.355 m) is added to a solution of 8-hydroxy-7-methyl-3-methylene-6,7-oxido-1-octene (59.7 g, 0.355 m) in methylene chloride (1 l) under nitrogen at 0° C. and the resulting mixture is then allowed to warm to room temperature. The mixture is washed with water (500 ml), the organic layer is dried (Na$_2$SO$_4$) and the solvent removed to give the crude dibromide (117.0 g).

A portion of the crude dibromide (57.2 g) in carbon tetrachloride (50 ml) is added to a solution of potassium acetate (59.8 g, 0.61 m) and Adogen 464 (15.0 g) in water at 60° C. The resulting mixture is stirred overnight, and then cooled to room temperature, diluted with ether (1 l) and washed with water (500 ml). The organic layer is dried (Na$_2$SO$_4$) and evaporated in vacuo to give the crude diacetate (64.0 g). The crude product is further purified by column chromatography on silica gel (2 kg, ethyl acetate/hexane 4:6) to give 1-acetoxy-8-hydroxy-7-methyl-3-acetoxymethyl-6,7-oxido-(E)-2-octene (9.5 g; 18%).

IR (neat) 3484, 1730 cm$^{-1}$;
NMR (CDCl$_3$)δ: 1.28 (s, 3H,

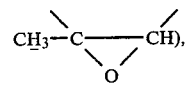

2.05 and 2.07 (each s, 6H,

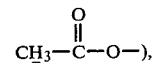

3.00 (t, J=6 Hz, 1H,

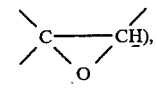

3.58 (bs, 2H, —C$\underline{H}_2$—OH), 4.50–4.73 (m, 4H,

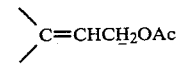

and

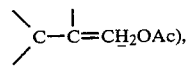

5.63 (t, J=7 Hz, 1H,

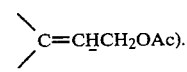

EXAMPLE L

1-Acetoxy-7-methyl-3-acetoxymethyl-6,7-oxido-8-tosyloxy-(E)-2-octene

Triethylamine (10 ml) and tosyl chloride (13.78 g, 0.072 m) are added to a solution of 1-acetoxy-8-hydroxy-7-methyl-3-acetoxymethyl-6,7-oxido-(E)-2-octene (10.34 g, 0.036 m) in dry tetrahydrofuran (300 ml). The resulting mixture is stirred at room temperature under nitrogen for 6 days and then diluted with ether (800 ml) and washed with 5% sodium bicarbonate solution (800 ml) and water (800 ml). The organic layer is dried (18.3 g). This material is purified by column chromatography on silica gel (600 g; ethyl acetate/hexane; 40:60) to give 1-acetoxy-7-methyl-3-acetoxymethyl-6,7-oxido-8-tosyloxy-(E)-2-octene (10.12 g, 64%).

IR (neat) 1730, 1595 cm$^{-1}$;

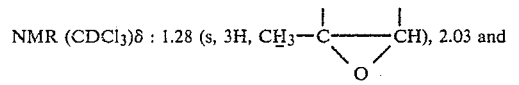

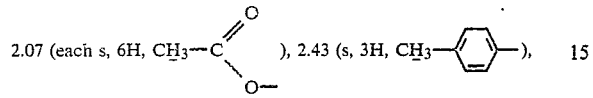

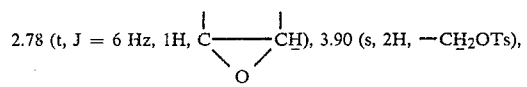

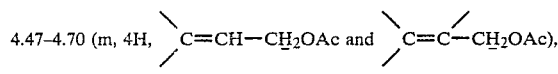

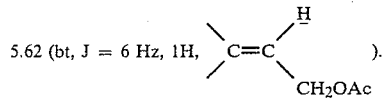

EXAMPLE M

7-Methyl-3-hydroxymethyl-6,7-oxido-8-tosyloxy-(E)-2-octen-1-ol

A mixture of 1-acetoxy-7-methyl-3-acetoxymethyl-6,7-oxido-8-tosyloxy-(E)-2-octene (4.0 g, 9.1 mole), methanol (150 ml), water (5 ml) and saturated potassium carbonate solution (5 ml) is stirred at room temperature for 2 hours. Most of the methanol is then removed in vacuo and the resulting mixture is extracted with ethyl acetate (3×20 ml). The combined organic layer is dried (MgSO$_4$) and evaporated in vacuo to give an oil (3.4 g). The oil is further purified by column chromatography on silica gel (20 g, isopropanol/chloroform 2.98) to give 7-methyl-3-hydroxymethyl-6,7-oxido-8-tosyloxy-(E)-2-octen-1-ol as a colorless oil (2.24 g, 69%).

IR (neat) 3424, 1597 cm$^{-1}$;

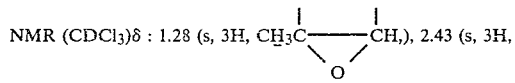

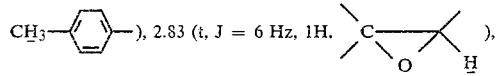

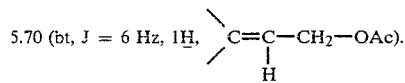

I claim:

1. The process for the preparation of a compound of the formula

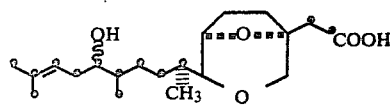

which comprises treating a compound of the formula

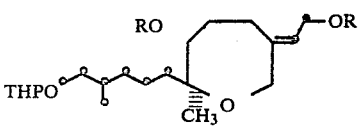

with a base to form a diol of the formula

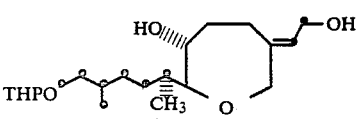

reacting the diol with an oxidizing agent to form an aldehyde of the formula

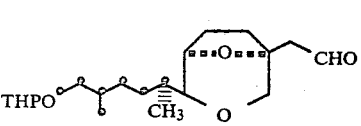

reacting the aldehyde with Jones reagent followed by treatment with diazomethane to form an ester of the formula

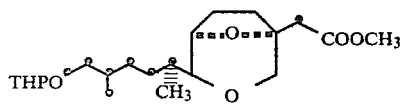

hydrolyzing the product formed with an acid to form an alcohol of the formula

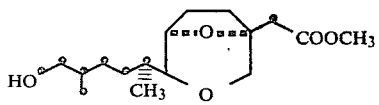

oxidizing the alcohol to form an aldehyde of the formula

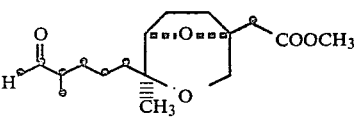

reacting the aldehyde with 3-methyl-3-butenyl magnesium bromide followed by reaction with an acid anhydride of the formula (R)$_2$O to form an ester of the formula

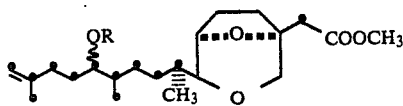

isomerizing the ester to form an isomer of the formula

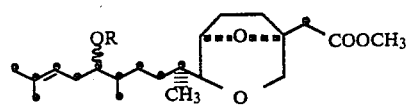

and reacting the isomer with a base, wherein R is lower alkanoyl having 2–5 carbon atoms and THP represents a tetrahydropyranyl group.

2. The process of claim 1 wherein R is an acetyl group.

3. The process of claim 1 wherein the base is potassium carbonate.

4. The process of claim 1 wherein the first oxidizing agent is manganese dioxide and the second oxidizing agent is chromium trioxide-pyridine.

5. The process of claim 1 wherein the hydrolyzing agent is acetic acid.

6. The process of claim 1 wherein the isomerization is carried out in the presence of p-toluenesulfonic acid.

7. The process of claim 1 wherein the acid anhydride is acetic anhydride.

8. A compound of the formula

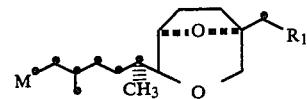

wherein M is a tetrahydropyran-2-yloxy group or an hydroxy group and $R_1$ is a —$COOCH_3$ or CHO group.

9. The compound of claim 8 wherein M is tetrahydropyran-2-yloxy and $R_1$ is —$COOCH_3$.

10. The compound of claim 8 wherein M is hydroxy and $R_1$ is —$COOCH_3$.

11. The compound of claim 8 wherein M is tetrahydropyran-2-yloxy and $R_1$ is —CHO.

* * * * *

UNITED STATES PATENT AND TRADEMARK OFFICE
CERTIFICATE OF CORRECTION

PATENT NO. : 4,237,054                    Page 1 of 2
DATED       : December 2, 1980
INVENTOR(S) : Robert H.K. Chen It is certified that error appears in the above—identified patent and that said Letters Patent is hereby corrected as shown below:

Column 16, line 12, the structure as shown is incorrect should appear as follows:

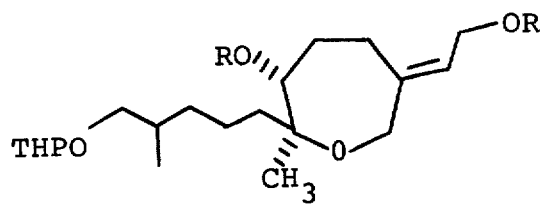

In the structures shown in
    Column 16, lines 5, 21, 30, 40 and 49,
    Column 17, lines 5 and 14 and
    Column 18, line 14

UNITED STATES PATENT AND TRADEMARK OFFICE
CERTIFICATE OF CORRECTION

PATENT NO. : 4,237,054
DATED : December 2, 1980
INVENTOR(S) : Robert H.K. Chen

It is certified that error appears in the above—identified patent and that said Letters Patent is hereby corrected as shown below:

the methyl group should appear on the ring as follows:

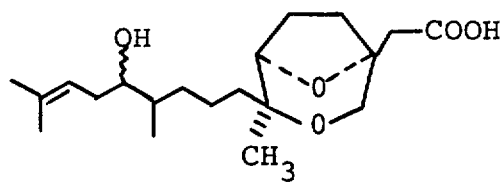

Signed and Sealed this

Tenth Day of August 1982

[SEAL]

Attest:

Attesting Officer

GERALD J. MOSSINGHOFF

Commissioner of Patents and Trademarks